United States Patent
Yamaguchi et al.

(10) Patent No.: US 8,609,116 B2
(45) Date of Patent: Dec. 17, 2013

(54) SOLID EMULSIFIED COSMETIC

(75) Inventors: Kanako Yamaguchi, Yokohama (JP); Yukiko Sato, Yokohama (JP); Hideo Hata, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 13/639,878

(22) PCT Filed: Mar. 15, 2011

(86) PCT No.: PCT/JP2011/056003
§ 371 (c)(1),
(2), (4) Date: Oct. 8, 2012

(87) PCT Pub. No.: WO2011/125424
PCT Pub. Date: Oct. 13, 2011

(65) Prior Publication Data
US 2013/0045260 A1  Feb. 21, 2013

(30) Foreign Application Priority Data

Apr. 7, 2010 (JP) ................. 2010-088630

(51) Int. Cl.
*A61K 9/00* (2006.01)
*A61K 8/58* (2006.01)

(52) U.S. Cl.
USPC ..................... 424/400; 424/70.121

(58) Field of Classification Search
USPC ................. 424/400, 70.12, 70.121
See application file for complete search history.

(56) References Cited

FOREIGN PATENT DOCUMENTS

| JP | 10-291914 | 11/1998 |
|----|-----------|---------|
| JP | 2000-063233 | 2/2000 |
| JP | 2000-086427 | 3/2000 |
| JP | 2005-272389 | 10/2005 |
| JP | 2006-056852 | 3/2006 |

OTHER PUBLICATIONS

Patent Abstracts of Japan, Publication No. 10-291914, 10 pages, 1998.
Patent Abstracts of Japan, Publication No. 2005-272389, 15 pages.
Patent Abstracts of Japan, Publication No. 2000-063233, 11 pages.
Patent Abstracts of Japan, Publication No. 2000-086427 11 pages.
Patent Abstracts of Japan, Publication No. 2006-056852 11 pages.
Ichiro Ono, et al, "Development of Silicones for Cosmetic Raw Materials", Fragrance Journal, May 15, 2003, vol. 31, No. 5, pp. 98-99, 2 pages.
PCT Notification of Transmittal of Translation of the International Preliminary Report on Patentability, International Application No. PCT/JP2011/056003, International Filing Date Mar. 15, 2011, 7 pages.

*Primary Examiner* — Michael G Hartley
*Assistant Examiner* — Robert Cabral
(74) *Attorney, Agent, or Firm* — Rankin, Hill & Clark LLP

(57) ABSTRACT

An object of the present invention is to provide a solid emulsified cosmetic that stably contains a large amount of a high refractive index silicone oil; gives a lustrous finish; and has a skin irregularity-correcting effect. Thus, a solid emulsified cosmetic of the present invention is characterized by comprising: (A) 4 to 18% by mass of a high refractive index silicone oil with a refractive index of 1.45 or higher at 25° C., (B) a (dimethicone/phenyl vinyl dimethicone)crosspolymer, (C) a hydrophobic or hydrophobically-treated powder, and (D) a wax.

20 Claims, No Drawings

SOLID EMULSIFIED COSMETIC

RELATED APPLICATIONS

This application claims the priority of Japanese Patent Application No. 2010-088630 filed on Apr. 7, 2010, which are incorporated herein by reference.

FIELD OF THE INVENTION

The present invention relates to a solid emulsified cosmetic, particularly to improvement in the finish and stability of the solid emulsified cosmetic.

BACKGROUND OF THE INVENTION

Recently, a solid emulsified cosmetic that is solidified with wax has been required not only to cover uneven color tone such as spots and freckles and skin irregularities such as pores and wrinkles, but also to give a lustrous finish. To realize this, it may be necessary to smooth out the skin surface (correct irregularities) by applying a solid emulsified cosmetic and impart luster to the skin by way of surface reflection of light by oil components contained in the cosmetic. In that case, in order to obtain luster by surface reflection, it is obvious that an oil component having a high refractive index, namely an oil component having a refractive index of 1.45 or higher at 25° C., is suitable. As representative oil components for cosmetics having such a characteristic, methyl phenyl silicone and caprylyl methicone, both of which are kinds of silicone oils, are known.

DISCLOSURE OF THE INVENTION

Problem to be Solved by the Invention

However, there have been problems that when a large amount of a silicone oil having such a high refractive index as described above is blended in a solid emulsified cosmetic, recrystallization of wax occurs, causing whitish alteration of the surface of the product. For this reason, while there are known solid emulsified cosmetics in which the high refractive index silicone oil is blended as one of the constituent oil components, the amount of the silicone oil blended is limited to about 2%. Blending of such a small amount of the oil component having a high refractive index could not provide at all a sufficient luster imparting effect.

Also, for example, Japanese unexamined patent application publication No. 2006-56852 describes a water-in-oil type emulsified cosmetic capable of correcting skin irregularities in which a volatile oil component, a non-volatile oil component, and a silicone elastic powder are blended at a specific ratio. However, considering the refractive indexes of the constituent oils, achieving an luster imparting effect in addition to correcting skin irregularities could not be expected so much, and further, considering the above problem of limitation of the blending amount, additional blending of a sufficient amount of high refractive index silicone oil to the cosmetic to give luster was also impossible.

The present invention was completed in view of the problems, and an object of the present invention is to provide a solid emulsified cosmetic that stably contains a large amount of a high refractive index silicone oil; gives a lustrous finish; and has a skin irregularity-correcting effect.

Means to Solve the Problem

The present inventors conducted an intensive study to solve the problems. As a result, they have found that by incorporating a high refractive index silicone oil with a refractive index of 1.45 or higher at 25° C. inside a (dimethicone/phenyl vinyl dimethicone) crosspolymer, the high refractive index silicone oil can be blended in a solid emulsified cosmetic in a large amount, and by additionally blending a powder, precipitation of wax in the cosmetic can be inhibited.

Further, they have found that, although it has been difficult for a composition containing a large amount of the high refractive index silicone oil to increase its hardness if an inorganic pigment is blended therein in an amount as in solid emulsified cosmetics, the hardness is increased by using a silicone-treated powder as the inorganic pigment. The present inventors completed the present invention based on the foregoing findings.

Thus, a solid emulsified cosmetic of the present invention is characterized by comprising:
(A) 4 to 18% by mass of a high refractive index slicone oil with a refractive index of 1.45 or higher at 25° C.,
(B) a (dimethicone/phenyl vinyl dimethicone)crosspolymer,
(C) a hydrophobic or hydrophobically-treated powder, and
(D) a wax.

Also, in the solid emulsified cosmetic, it is preferable that (A) the high refractive index silicone oil with a refractive index of 1.45 or higher at 25° C. is methyl phenyl silicone and/or caprylyl methicone.

Also, in the solid emulsified cosmetic, it is preferable that a combination ratio (B):(A) is 1:9 to 3:7.

Also, in the solid emulsified cosmetic, it is preferable that (A) the high refractive index silicone oil with a refractive index of 1.45 or higher at 25° C. is blended in an amount of 8 to 18% by mass.

Also, in the solid emulsified cosmetic, it is preferable that (C) the hydrophobic or hydrophobically-treated powder is a silicone-treated powder.

Also, in the solid emulsified cosmetic, it is preferable that a mean major-axis length of a primary particle of (C) the hydrophobic or hydrophobically-treated powder is 0.05 to 0.2 µm.

Also, a method for imparting a lustrous finish and an irregularity-correcting effect to a solid emulsified cosmetic is characterized by comprising:
blending (A) 4 to 18% by mass of a high refractive index silicone oil with a refractive index of 1.45 or higher at 25° C.,
(B) a (dimethicone/phenyl vinyl dimethicone) crosspolymer,
(C) a hydrophobic or hydrophobically-treated powder, and
(D) a wax
into the solid emulsified cosmetic.

Effect of the Invention

According to the present invention, a stable solid emulsified cosmetic from which a wax component is not recrystallized over time can be obtained. Further, because a large amount of a high refractive index silicone oil can be blended in the solid emulsified cosmetic of the present invention, pit can achieve both an excellent effect of imparting luster to the skin and an excellent skin irregularity-correcting effect.

DESCRIPTION OF THE PREFERRED EMBODIMENT

Hereinbelow, preferred embodiments of the present invention will be described in detail.

The present invention contains, as essential components, (A) a silicone oil having a refractive index of 1.45 or higher at 25° C., (B) a (dimethicone/phenyl vinyl dimethicone) crosspolymer, (C) a hydrophobic and hydrophobically-treated powder, and (D) a wax.

(A) the silicone oil having a refractive index of 1.45 or higher at 25° C., which is the component responsible for imparting luster and correcting irregularities, is provided in the form of a mixed gel with (B) the (dimethicone/phenyl vinyl dimethicone) crosspolymer, and thereby can be blended into a solid emulsified cosmetic containing (D) the wax, in a large amount and in a stable manner. Further, in the present invention, by incorporation of (C) the powder, the surface precipitation of the component (D) due to incorporation of the component (A) is inhibited.

First of all, each of the components will be described.

(A) Silicone Oil with a Refractive Index of 1.45 or Higher at 25° C.

The component (A) of the present invention is a silicone oil having a refractive index of 1.45 or higher at 25° C., preferably methyl phenyl silicone and/or caprylyl methicone, more preferably methyl phenyl silicone.

The methyl phenyl silicone is linear dimethylpolysiloxane in which a methyl group is partially substituted by a phenyl group and/or a phenyl group and a trimethylsiloxy group, and no particular limitation is imposed on the number of moles of each of a phenyl group and/or a phenyl group and a trimethylsiloxy group added. Also, methyl phenyl silicone used as the component (A) may be composed of methyl phenyl silicone having a single structure or a mixture of methyl phenyl silicones having different structures; however, the refractive index (25° C.) is 1.45 or higher as a mixture. If the refractive index is less than 1.45, the luster imparting effect of the solid emulsified cosmetic may not be sufficiently obtained.

As such methyl phenyl silicone, for example, as trimethyl pentaphenyl polysiloxane, FZ-3156 [refractive index: 1.575] manufactured by Nippon Unicar Company Limited; as diphenylsiloxy phenyl trimethicone, KF-56 [refractive index: 1.498] and KSG-18A [refractive index: 1.495] manufactured by Shin-Etsu Chemical Co., Ltd.; as diphenyl dimethicone, KF-54 [refractive index: 1.505] manufactured by Shin-Etsu Chemical Co., Ltd.; and as methyl phenyl polysiloxane, methyl phenyl polysiloxane (500 cs) [refractive index: 1.535] manufactured by Dow Corning Toray Co., Ltd are commercially available, and these products can be preferably used. Among them, diphenylsiloxy phenyl trimethicone is preferably used, and particularly, KSG-18A, which is a mixed gel of diphenylsiloxy phenyl trimethicone and a (dimethicone/phenyl vinyl dimethicone) crosspolymer, is more preferable because it can also serve as the component (B) of the present invention to be described later and be blended simultaneously. Also, the commercial products may be used in an appropriate combination.

Also, examples of commercially available caprylyl methicone include FZ-3196 and SS-3408 [refractive index: 1.413] manufactured by Dow Corning Toray Co., Ltd., and these products are preferably used.

In the solid emulsified cosmetic of the present invention, the amount of (A) the silicone oil having a refractive index of 1.45 or higher at 25° C. to be blended is 4 to 18% by mass, more preferably 8 to 18% by mass of the composition. If the blending amount is less than 4% by mass, it is difficult to impart a lustrous finish to the solid emulsified cosmetic. Also, if the component (A) is blended in a blending amount of more than 18% by mass, precipitation of wax in the surface of the composition cannot be inhibited.

(B) (Dimethicone/Phenyl Vinyl Dimethicone) Crosspolymer

The (dimethicone/phenyl vinyl dimethicone) crosspolymer used in the present invention is a three-dimensional crosslinked polymer resulting from the polymerization reaction between cross-linked methyl polysiloxane and phenyl-modified silicone (phenyl vinyl dimethicone). Although the crosspolymer is present as a fine particle by itself, it turns into a gel by absorbing and swelling with silicone oil (solvent). Namely, it is assumed that a large amount of a silicone oil having a refractive index of 1.45 or higher at 25° C., which is the component (A), can be stably blended in the solid emulsified cosmetic because the silicone oil is incorporated inside the three-dimensional network structure of the crosspolymer.

Further, a crosspolymer, which is the component (B), gives smooth feel upon application with good spreadability by turning into a soft gel by mixing with the component (A). This is considered to contribute in no small part to correction and the smoothing out of the irregularities on the skin surface by application of the solid emulsified cosmetic of the present invention, and moreover, to even coating of the skin with the component (A). Accordingly, the number of the crosslinking points in the (dimethicone/phenyl vinyl dimethicone) crosspolymer is preferably small enough to allow the mixture with the component (A) to turn into a gel.

Also, the refractive index (25° C.) of (B) the (dimethicone/phenyl vinyl dimethicone) crosspolymer is preferably high similarly to the component (A), and preferably particularly 1.40 or higher. Even in a case when the component (A) has a high refractive index, if the refractive index of the component (B) that is present with the component (A) is low, a satisfactory luster imparting effect may not be obtained.

The (dimethicone/phenyl vinyl dimethicone) crosspolymer used here is not limited to a synthetic product by the polymerization reaction, and particularly, a commercially available product, KSG-18A manufactured by Shin-Etsu Chemical Co., Ltd. is preferably used. As described above, because KSG-18A is in the form of a mixed gel composed of about 84% diphenylsiloxy phenyl trimethicone and about 16% (dimethicone/phenyl vinyl dimethicone) crosspolymer, it can be blended as the component (A) and the component (B) of the present invention.

In the solid emulsified cosmetic of the present invention, the amount of (B) the (dimethicone/phenyl vinyl dimethicone) crosspolymer blended can be set within such a range that the combination ratio relative to (A) the silicone oil having a refractive index of 1.45 or higher at 25° C., (B):(A), is 1:9 to 3:7. Accordingly, the amount of the component (B) blended is preferably 0.3 to 6% by mass of the composition.

Namely, for example, if KSG-18A is solely used as the component (A) and the component (B), the combination ratio is 1.6:8.4. When it is desirable to further increase the ratio of the amount of the component (A), the ratio can be adjusted by blending only the component (A) (for example, KF-56) in such a range that the total amount of the component (A) is 4 to 18% by mass.

(C) Hydrophobic or Hydrophobically-treated Powder

The excellent luster imparting and skin irregularity-correcting effects of the solid emulsified cosmetic of the present invention can be achieved by incorporation of the component (A) together with the component (B). Further, recrystallization of wax caused by incorporation of the component (A) can be greatly reduced by intake of the component (A) by the component (B). In view of the above, in the present invention, recrystallization of wax is completely inhibited by further blending (C) the hydrophobic or hydrophobically-treated powder.

In the present invention, from among inorganic powders, organic powders, metal powders, and the like that are normally used for cosmetics, quasi drugs, and the like, those that are hydrophobic or have been subjected to hydrophobic treatment can be used.

Here, the term "a hydrophobic or hydrophobically-treated powder" refers to a powder that has low affinity to water. Particularly, a hydrophobic powder is a powder that itself exhibits a low affinity to water, while a hydrophobically-treated powder refers to a powder having high affinity to water that has acquired hydrophobicity through surface treatment.

Examples of the hydrophobic powder include, as an inorganic powder, an organopolysiloxane elastomer spherical powder or a composite spherical powder based on the former powder; and as an organic powder, a polyamide resin powder (nylon powder), a polyethylene powder, a poly methyl methacrylate powder, a styrene/acrylic acid copolymer resin powder, a benzoguanamine resin powder, a polytetrafluoroethylene powder, a cellulose powder, a polyurethane spherical powder, or a composite spherical powder based on the former spherical powder. Particularly, in the present invention, an oil-absorbing powder is preferable.

A hydrophobically-treated powder is obtainable by treating the surface of any powder normally used for cosmetics, quasi drugs, and the like with a substance such as a higher fatty acid, an oil, a wax, a silicone compound, a fluorine compound, a hydrocarbon, a surfactant, and a dextrin fatty acid ester. The method of hydrophobic treatment is not particularly limited, and publicly known technique can be appropriately applied.

In the present invention, particularly, titanium oxide with excellent oil absorptivity is preferably used as a hydrophobically-treated powder because it absorbs methyl phenyl silicone that is not incorporated in the crosspolymer and has a high inhibitory effect on precipitation of wax.

Also, (C) the powder of the present invention is preferably a mid-sized particle having a mean major-axis length of a primary particle diameter of 0.05 to 0.2 μm as measured by dynamic light scattering, by analysis of a scanning electron microscopic image (SEM), and the like. Further, the specific surface area of (C) the powder is preferably 10 m$^2$/g or more, more preferably 20 m$^2$/g or more. Also, although the upper limit of the specific surface area is not limited, from the viewpoint of usability, the specific surface area is preferably 150 m$^2$/g or less. When the specific surface area is too small as for a pigment-grade powder (a powder generally having a mean major-axis length of a primary particle diameter of 0.25 to 0.3 μm), enhanced inhibition of recrystallization of wax by incorporation of a powder may be insufficient.

Also, in the present invention, the solid cosmetic may not be solidified to the desired hardness due to incorporation of a gel substance composed of the components (A) and (B). In such a case, in the present invention, it is preferable to attempt to increase the hardness of the cosmetic by blending the hydrophobic or hydrophobically-treated powder. In attempting to increase the hardness, particularly, a silicone-treated powder is preferably used as the component (C). When a powder treated with other than silicone is used, a sufficient increase in hardness may not be expected.

Here, in the present invention, the term "solid" in the solid emulsified cosmetic means a state in which a composition does not exhibit fluidity at a temperature of 50° C. or below. More specifically, for example, it means that the hardness γ expressed by the following formula that is measured by using a publicly known measurement device such as a rheometer (the product of FUDO kougyou, Inc.) is 30 or more.

$$\gamma = (G^*L)/(1^*a)(dyn/cm^2)$$

(wherein, G: stress measured (gr)*980 dyn, L: sample thickness (mm), 1: compression distance (mm), a: cross-sectional area of a needle (cm$^2$))
(Measurement Condition)
Load: 200 g, diameter of a needle: 5.6ϕ), rate of needle insertion: 2 cm/min, distance of needle insertion: 1 mm, measurement temperature: 37° C.

In the present invention, even an untreated powder can satisfy the hardness criteria; however, for example, by using a higher fatty acid-treated powder or a silicone-treated powder, the hardness γ can be increased to 40 or above, and particularly by using a silicone-treated powder, the hardness γ can be increased to 50 or above. By doing so, the impact resistance of the cosmetic against fall can be improved, and the range of choices for usage and form of the cosmetic can be expanded.

Examples of the silicone-treated powder used in the present invention include a powder that has been subjected to surface treatment with high-viscosity silicone or a powder, the surface of which is coated with silicone resin that has been reacted with alkyl hydrogen polysiloxane. The powder can be treated with one or two or more kinds of silicones.

The amount of (C) the powder to be blended is, relative to the amount of (A) the silicone oil having a refractive index of 1.45 or higher at 25° C. to be blended, preferably 0.1 to 1.7 (powder/silicone oil having a refractive index of 1.45 or higher at 25° C.).

(D) Wax

Also, a wax is blended in the solid emulsified cosmetic of the present invention as a solidifying agent of the composition.

The wax used for the solid emulsified cosmetic of the present invention is an oil that contains the higher fatty acid ester component and is solid or semi-solid at normal temperature, which normally contains a carboxylic acid ester composed of a moiety derived from a higher fatty acid having 18 to 34 carbon atoms and a moiety derived from a higher fatty alcohol having 18 to 44 carbon atoms. These fatty acid- and fatty alcohol-derived moieties may be linear or branched, or saturated or unsaturated; however, they are more preferably saturated aliphatic groups. It should be noted that a naturally occurring wax normally includes, in addition to the fatty acid esters, free fatty acid, free alcohol, or hydrocarbon, and a wax containing these other components may also be used as the wax of the present invention.

Examples of waxes, which can be used in the solid emulsified cosmetic of the present invention, specifically include beeswax, candelilla wax, cotton wax, carnauba wax, bayberry wax, insects wax, spermaceti, montan wax, bran wax, lanolin, capok wax, Japan wax, lanolin acetate, liquid lanolin, sugar cane wax, isopropyl lanolate, hexyl laurate, reduced lanolin, jojoba wax, lanolin wax, shellac wax, beeswax, microcrystalline wax, paraffin wax, POE lanolin alcohol ethers, POE lanolin alcohol acetates, POE cholesterol ethers, lanolin fatty acid polyethylene glycol, fatty acid glycerides, hardened castor oil, Vaseline, and POE hydrogenated lanolin alcohol ethers. A mixture of these waxes can be used, and these waxes can also be mixed with other solid or liquid oil components when used.

The amount of the wax blended in the present invention is preferably 1 to 8% by mass of the composition. When the blending amount is less than 1% by mass, solidification of the composition is insufficient, and when the blending amount is more than 8% by mass, application of the content onto a sponge becomes difficult.

Also, the solid emulsified cosmetic of the present invention can contain, in addition to (A) the silicone oil having a refractive index of 1.45 or higher at 25° C., which is the essential component, other oil components used for cosmetics, quasi drugs, and the like, for example, hydrocarbon oil, higher fatty acid, higher alcohol, synthetic ester oil, silicone oil, liquid oil, and solid oil within such a range that the effect of the present invention is not impaired.

Examples of hydrocarbon oil include isohexadecane, liquid paraffin, ozocerite, scualane, pristine, paraffin, ceresin, squalene, vaseline and microcrystalline wax.

Examples of higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA) and docosahexaenoic acid (DHC).

Examples of higher alcohol include linear alcohol (e.g. lauryl alcohol, cetyl alcohol, stearic alcohol, behenyl alcohol, myristyl alcohol, oleyl alcohol and cetostearyl alcohol); and branched-chain alcohol (e.g. monostearyl glycerin ether (batyl alcohol), 2-decyl tetradecinol, lanoline alconol, cholesterol, phytosterol, hexyldodecanol, isostearyl alcohol and octyl dodecanol).

Examples of synthetic ester oil include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentylglycol dicaprate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri(2-ethylhexanoate), glyceryl trioctanoate, glyceryl triisopalmitate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of silicone oil include linear polysiloxane (e.g. dimethylpolysiloxane and diphenylpolysiloxane); cyclic polysiloxane (e.g. octamethylcyclotetrasiloxane, decamethylcyclopentasiloxane and dodecamethylcyclohexasiloxane); silicone resin forming three-dimensional network structure; silicone rubber; various kinds of modified polysiloxane (e.g. amino modified polysiloxane, polyether modified polysiloxane, alkyl modified polysiloxane polyether/alkyl co-modified polysiloxane, fluorine modified polysiloxane, polyoxyethylene/polyoxypropylene co-modified polysiloxane, aminoglycol modified polysiloxane, aminophenyl modified polysiloxane, carbinol modified polysiloxane, polyglycerin modified polysiloxane and polyglycerin/alkyl co-modified polysiloxane); dimethiconol; and acrylic silicone.

Examples of liquid oil include avocado oil, camellia oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japanese tung oil, jojoba oil, germ oil and triglycerin.

The amounts of the above other oil components blended are generally about 5 to 50% by mass of the composition of the present invention. When the oil components are blended in an amount of 5% by mass or more, the composition can be easily mixed homogeneously; however, when the blending amount is more than 50%, precipitation of wax may occur.

The solid emulsified cosmetic of the present invention can contain, in addition to the oil components, other components normally used for cosmetics, quasi drugs, and the like within such a range that the effect of the present invention is not impaired. Examples of such components include powder, anionic surfactant, cationic surfactant, ampholytic surfactant, non-ionic surfactant, dispersant, stabilizing agent, humectant, water-soluble polymer, thickener, coating agent, ultraviolet absorber, sequestrant, lower alcohol, polyol, sugar, amino acid, organic amine, high molecular emulsion, pH adjuster, skin nutritional supplement, vitamin, preservative, antioxidant, auxiliary antioxidant, perfume and water.

Examples of the production method for the solid emulsified cosmetic of the present invention include a method involving:

blending (A) the silicone oil having a refractive index of 1.45 or higher at 25° C. and (B) the (dimethicone/phenyl vinyl dimethicone) crosspolymer into the oil components other than (A), to form a gel;

mixing the gel with (D) the wax melted by heating, in which (C) the hydrophobic and hydrophobically-treated powder are dispersed, by stirring; and emulsifying the resulting product with other raw materials.

However, as long as a solid emulsified cosmetic having the effect of the present invention can be obtained, no particular limitation is imposed on the production method.

Also, although specific usage of the solid emulsified cosmetic of the present invention is not particularly limited, it can be used for, for example, a make-up cosmetic such as a foundation, a make-up base, a concealer, a face powder, a blush, a lip stick, an eye shadow, an eyeliner, a mascara, and a sunscreen. Particularly, in view of high demand for a lustrous finish and a skin irregularity-correcting effect, it is effectively used for a foundation, a make-up base, a concealer, and the like.

EXAMPLES

Hereinbelow, the present invention will be described in more detail with reference to Examples. The present invention is not limited by these Examples. Unless otherwise specified, the blending amount is indicated by % by mass.

First of all, the effect test method and evaluation criteria used in the present Examples will be described.

(1) Precipitation of Wax

An accelerated test was performed under harsh conditions, which included storing the composition for two weeks under conditions of changing a temperature at which the composition was held from 5° C. to 45° C. with a period of 12 hours. The state of recrystallization of wax after the test was confirmed and evaluated based on the following criteria.

⊚: There is no change compared to before the test.
○: Very faint whitish alteration of the surface of the composition is confirmed.
Δ: Wax is recrystallized and whitish alteration of the surface of the composition is confirmed.
X: Wax is recrystallized and whitish alteration of the surface of the composition is clearly confirmed.

(2) Lustrous Finish

Ten cosmetic panelists applied the cosmetic of each Example to their faces and organoleptically evaluated the luster of the skin after application, and then evaluated the cosmetic according to the following criteria.

⊚: Eight or more out of 10 judged that the skin was lustrous after application.
○: Five to seven, or more out of 10 judged that the skin was lustrous after application.

Δ: Two to four out of 10 judged that the skin was lustrous after application.
X: One or none out of 10 judged that the skin was lustrous after application.

(3) Irregularity-Correcting Effect

Five cosmetic panelists applied the cosmetic of each Example to their faces and organoleptically evaluated if the cosmetic covered uneven color tone such as spots and freckles and gave an even finish, and then evaluated the cosmetic according to the following criteria.
○: Four or more out of five judged that the cosmetic had an irregularity-correcting effect.
Δ: Two to three out of five judged that the cosmetic had an irregularity-correcting effect.
X: One or none out of five judged that the cosmetic had an irregularity-correcting effect.

First of all, with regard to the solid emulsified cosmetic having the formulation as shown in Table 1 below, a combination of an oil component and a crosspolymer was studied. It should be noted that the refractive index of each oil component at 25° C. was as follows; diphenylsiloxy phenyl trimethicone, 1.495, dimethyl polysiloxane, 1.406, and decamethyl cyclopentasiloxane, 1.396.

particle of 0.03 to 0.04 μm, a mean major-axis length of a primary particle of 0.09 to 0.10 μm, and an aspect ratio (major axis/minor axis) of 2 to 4 was used.

(Production Method)

Diphenylsiloxy phenyl trimethicone and a (dimethicone/phenyl vinyl dimethicone) crosspolymer or a (dimethicone/vinyl dimethicone) crosspolymer were blended into the oil components other than diphenylsiloxy phenyl trimethicone. The resulting mixture was mixed with a wax melted by heating, in which a powder was dispersed, by stirring. The resulting mixture was emulsified with a mixture of other components to give a solid emulsified cosmetic.

As shown in Table 1, a lustrous finish was obtained in Test Examples 1-1, 1-2, and 1-4, in which a silicone oil having a refractive index of 1.5 or higher (methyl phenyl silicone) was blended. Meanwhile, absolutely no luster imparting effect was obtained in Test Example 1-3, in which dimethyl polysiloxane, which had a low refractive index, was blended as the main component instead of methyl phenyl silicone.

Also, no recrystallization of wax was observed in Test Examples 1-1 and 1-2, in which a (dimethicone/phenyl vinyl dimethicone) crosspolymer was blended together with methyl phenyl silicone.

TABLE 1

|  | Test Example 1-1 | Test Example 1-2 | Test Example 1-3 | Test Example 1-4 |
|---|---|---|---|---|
| (Oil component) | | | | |
| Diphenylsiloxy phenyl trimethicone | 17.64 | 8.82 | — | 17.64 |
| Dimethylpolysiloxane | | 8.82 | 17.64 | — |
| Decamethyl cyclopentasiloxane | 30.65 | 30.65 | 30.65 | 34.01 |
| (Surfactant) | | | | |
| PEG-10 dimethicone | 2 | 2 | 2 | 2 |
| (Dispersant) | | | | |
| Sorbitan sesquiisostearate | 1 | 1 | 1 | 1 |
| Distearyldimonium chloride | 0.2 | 0.2 | 0.2 | 0.2 |
| Palmitic acid | 0.15 | 0.15 | 0.15 | 0.15 |
| (Stabilizing agent) | | | | |
| Tocopherol | 0.02 | 0.02 | 0.02 | 0.02 |
| (Elastomer) | | | | |
| (Dimethicone/phenyl vinyl dimethicone) crosspolymer | 3.36 | 3.36 | — | — |
| (Dimethicone/vinyl dimethicone) crosspolymer | — | — | 3.36 | — |
| (Wax) | | | | |
| Microcrystalline wax | 0.8 | 0.8 | 0.8 | 0.8 |
| Paraffin wax | 3.5 | 3.5 | 3.5 | 3.5 |
| (Powder) | | | | |
| Silicone-treated iron oxide | 2.75 | 2.75 | 2.75 | 2.75 |
| Silicone-treated pigment-grade titanium oxide | 12 | 12 | 12 | 12 |
| Silicone-treated mid-sized titanium oxide | 7 | 7 | 7 | 7 |
| (Water) | | | | |
| Deionized water | 15.08 | 15.08 | 15.08 | 15.08 |
| (Humectant) | | | | |
| Dipropylene glycol | 3.5 | 3.5 | 3.5 | 3.5 |
| (Preservative) | | | | |
| Phenoxyethanol | 0.35 | 0.35 | 0.35 | 0.35 |
| Crosspolymer : Linear silicone | 1.6:8.4 | 1.6:8.4 | 1.6:8.4 | — |
| (1) Precipitation of wax | ◎ | ◎ | ◎ | X |
| (2) Lustrous finish | ○ | ○ | X | ○ |
| (3) Irregularity-correcting effect | ○ | ○ | Δ | Δ |

*As the silicone-treated mid-sized titanium oxide particle in Table 1, a silicone-treated, spindle-shaped fine titanium oxide particle having a mean minor-axis length of a primary Accordingly, in the present invention, it is preferable to blend a silicone oil having a refractive index of 1.45 or higher at 25° C. and a (dimethicone/phenyl vinyl dimethicone) crosspolymer.

Subsequently, with regard to the solid emulsified cosmetic having the formulation as shown in Table 2 below, the amount of a high refractive index silicone oil to be added was studied. It should be noted that the refractive index of each oil at 25° C. was as follows; diphenylsiloxy phenyl trimethicone, 1.495 and decamethyl cyclopentasiloxane, 1.396.

As shown in Table 2, both luster imparting effect and irregularity-correcting effect were accomplished in Test Examples 2-2 to 2-4, in which diphenylsiloxy phenyl trimethicone was blended in an amount of 4% by mass or more. Particularly, in Test Examples 2-3 and 2-4, in which diphenylsiloxy phenyl trimethicone was blended in an amount of 8% by mass or more, a high luster imparting effect was observed. Meanwhile, neither of the effects was observed in Test Example 2-1, in which a small amount of diphenylsiloxy phenyl trimethicone was blended.

TABLE 2

|  | Test Example 2-1 | Test Example 2-2 | Test Example 2-3 | Test Example 2-4 |
|---|---|---|---|---|
| (Oil component) | | | | |
| Diphenylsiloxy phenyl trimethicone | 0.84 | 4.2 | 8.4 | 17.6 |
| Decamethyl cyclopentasiloxane | 50.65 | 46.65 | 41.65 | 30.65 |
| (Surfactant) | | | | |
| PEG-10 dimethicone | 2 | 2 | 2 | 2 |
| (Dispersant) | | | | |
| Sorbitan sesquiisostearate | 1 | 1 | 1 | 1 |
| Distearyldimonium chloride | 0.2 | 0.2 | 0.2 | 0.2 |
| Palmitic acid | 0.15 | 0.15 | 0.15 | 0.15 |
| (Stabilizing agent) | | | | |
| Tocopherol | 0.02 | 0.02 | 0.02 | 0.02 |
| (Elastomer) | | | | |
| (Dimethicone/phenyl vinyl dimethicone) crosspolymer | 0.16 | 0.8 | 1.6 | 3.4 |
| (Wax) | | | | |
| Microcrystalline wax | 0.8 | 0.8 | 0.8 | 0.8 |
| Paraffin wax | 3.5 | 3.5 | 3.5 | 3.5 |
| (Powder) | | | | |
| Silicone-treated iron oxide | 2.75 | 2.75 | 2.75 | 2.75 |
| Silicone-treated pigment-grade titanium oxide | 12 | 12 | 12 | 12 |
| Silicone-treated mid-sized titanium oxide | 7 | 7 | 7 | 7 |
| (Water) | | | | |
| Deionized water | 15.08 | 15.08 | 15.08 | 15.08 |
| (Humectant) | | | | |
| Dipropylene glycol | 3.5 | 3.5 | 3.5 | 3.5 |
| (Preservative) | | | | |
| Phenoxyethanol | 0.35 | 0.35 | 0.35 | 0.35 |
| Combination ratio (B):(A) | 1.6:8.4 | 1.6:8.4 | 1.6:8.4 | 1.6:8.4 |
| (1) Precipitation of wax (2W) | ◎ | ◎ | ◎ | ◎ |
| (2) Lustrous finish | X | ○ | ◎ | ◎ |
| (3) Irregularity-correcting effect | X | ○ | ○ | ○ |

*As the silicone-treated mid-sized titanium oxide particle in Table 2, a silicone-treated, spindle-shaped fine titanium oxide particle having a mean minor-axis length of a primary particle of 0.03 to 0.04 μm, a mean major-axis length of a primary particle of 0.09 to 0.10 μm, and an aspect ratio (major axis/minor axis) of 2 to 4 was used.

(Production Method)

Diphenylsiloxy phenyl trimethicone and a (dimethicone/phenyl vinyl dimethicone) crosspolymer were mixed with the oil components other than diphenylsiloxy phenyl trimethicone. The resulting mixture was mixed with a wax melted by heating, in which a powder was dispersed, by stirring. The resulting mixture was emulsified with a mixture of other components to give a solid emulsified cosmetic.

Also, as a result of further study, there was a tendency of precipitation of wax in the Example in which the amount of diphenylsiloxy phenyl trimethicone added was more than 18% by mass.

Accordingly, in the present invention, the additive amount of a high refractive index silicone oil with a refractive index of 1.45 or higher at 25° C. is preferably 4 to 18% by mass, more preferably 8 to 18% by mass.

Subsequently, with regard to the solid emulsified cosmetic having the formulation as shown in Table 3 below, the combination ratio between the (dimethicone/phenyl vinyl dimethicone) crosspolymer and methyl phenyl silicone was studied. It should be noted that the refractive index of each oil at 25° C. was as follows; diphenylsiloxy phenyl trimethicone, 1.495 and decamethyl cyclopentasiloxane, 1.396.

TABLE 3

|  | Test Example 3-1 | Test Example 3-2 | Test Example 3-3 | Test Example 3-4 |
|---|---|---|---|---|
| (Oil component) | | | | |
| Diphenylsiloxy Phenyl trimethicone | 17 | 17 | 17 | 17 |
| Decamethyl cyclopentasiloxane | 33.65 | 32.65 | 31.65 | 29.65 |
| (Surfactant) | | | | |
| PEG-10 dimethicone | 2 | 2 | 2 | 2 |
| (Dispersant) | | | | |
| Sorbitan sesquiisostearate | 1 | 1 | 1 | 1 |
| Distearyldimonium chloride | 0.2 | 0.2 | 0.2 | 0.2 |
| Palmitic acid | 0.15 | 0.15 | 0.15 | 0.15 |
| (Stabilizing agent) | | | | |
| Tocopherol | 0.02 | 0.02 | 0.02 | 0.02 |
| (Elastomer) | | | | |
| (Dimethicone/phenyl vinyl dimethicone) crosspolymer | 1 | 2 | 3 | 5 |
| (Wax) | | | | |
| Microcrystalline wax | 0.8 | 0.8 | 0.8 | 0.8 |
| Paraffin wax | 3.5 | 3.5 | 3.5 | 3.5 |
| (Powder) | | | | |
| Silicone-treated iron oxide | 2.75 | 2.75 | 2.75 | 2.75 |
| Silicone-treated pigment-grade titanium oxide | 12 | 12 | 12 | 12 |
| Silicone-treated mid-sized titanium oxide | 7 | 7 | 7 | 7 |
| (Water) | | | | |
| Deionized water | 15.08 | 15.08 | 15.08 | 15.08 |
| (Humectant) | | | | |
| Dipropylene glycol | 3.5 | 3.5 | 3.5 | 3.5 |
| (Preservative) | | | | |
| Phenoxyethanol | 0.35 | 0.35 | 0.35 | 0.35 |
| Combination ratio (B):(A) | 0.5:9.5 | 1:9 | 1.5:8.5 | 2.3:7.7 |
| (1) Precipitation of wax (2W) | Δ | ○ | ◎ | ○ |
| (2) Lustrous finish | ◎ | ◎ | ◎ | ○ |
| (3) Irregularity-correcting effect | Δ | ○ | ○ | ○ |

\* As the silicone-treated mid-sized titanium oxide particle in Table 3, a silicone-treated, spindle-shaped fine titanium oxide particle having a mean minor-axis length of a primary particle of 0.03 to 0.04 μm, a mean major-axis length of a primary particle of 0.09 to 0.10 μm, and an aspect ratio (major axis/minor axis) of 2 to 4 was used.

(Production Method)

Diphenylsiloxy phenyl trimethicone and a (dimethicone/phenyl vinyl dimethicone) crosspolymer was mixed with the oil components other than diphenylsiloxy phenyl trimethicone. The resulting mixture was mixed with a wax that was melted by heating, in which a powder was dispersed, by stirring. The resulting mixture was emulsified with a mixture of other components to give a solid emulsified cosmetic.

As shown in Table 3, in Test Examples 3-2 to 3-4 whose combination ratio of (B) (dimethicone/phenyl vinyl dimethicone) crosspolymer to (A) methyl phenyl silicone, i.e. (B):(A), fell within a range of 1:9 to 3:7, both luster imparting effect and irregularity-correcting effect were exhibited, and recrystallization of wax was hardly observed.

Meanwhile, in Test Example 3-1 whose combination ratio, (B):(A), was out of the range, the product was in the acceptable range for use but recrystallization of wax was observed.

Accordingly, in the present invention, it is preferable that the combination ratio of (B) (dimethicone/phenyl vinyl dimethicone) crosspolymer to (A) methyl phenyl silicone, (B):(A), is in the range of 1:9 to 3:7.

Further, with regard to the solid emulsified cosmetic having the formulation as shown in Table 4 below, the surface treatment of titanium oxide, which was the powder component, was studied. In Table 4, the hardness in (4) is a value obtained by measuring the hardness of the cosmetic of each Test Example by the previously described measurement method.

TABLE 4

|  | Test Example 4-1 | Test Example 4-2 | Test Example 4-3 | Test Example 4-4 |
|---|---|---|---|---|
| (Oil component) | | | | |
| Diphenylsiloxy phenyl trimethicone | 17.64 | 17.64 | 17.64 | 17.64 |
| Decamethyl cyclopentasiloxane | 30.65 | 30.65 | 30.65 | 29.93 |
| (Surfactant) | | | | |
| PEG-10 dimethicone | 2 | 2 | 2 | 2 |

TABLE 4-continued

| | Test Example 4-1 | Test Example 4-2 | Test Example 4-3 | Test Example 4-4 |
|---|---|---|---|---|
| (Dispersant) | | | | |
| Sorbitan sesquiisostearate | 1 | 1 | 1 | 1 |
| Distearyldimonium chloride | 0.2 | 0.2 | 0.2 | 0.2 |
| Palmitic acid | 0.15 | 0.15 | 0.15 | 0.15 |
| (Stabilizing agent) | | | | |
| Tocopherol | 0.02 | 0.02 | 0.02 | 0.02 |
| (Elastomer) | | | | |
| (Dimethicone/phenyl vinyl dimethicone) crosspolymer | 3.36 | 3.36 | 3.36 | 3.36 |
| (Wax) | | | | |
| Microcrystalline wax | 0.8 | 0.8 | 0.8 | 0.8 |
| Paraffin wax | 3.5 | 3.5 | 3.5 | 3.5 |
| (Powder) | | | | |
| Silicone-treated iron oxide | 2.75 | 2.75 | 2.75 | 2.75 |
| Silicone-treated pigment-grade titanium oxide | 12 | 12 | 12 | 12 |
| Silicone-treated mid-sized titanium oxide | 7 | — | — | — |
| Silicone resin-coated mid-sized titanium oxide | — | 7 | — | — |
| Stearic acid-treated mid-sized titanium oxide (Specific surface area: 38 m²/g) | — | — | 7 | — |
| (Water) | | | | |
| Deionized water | 15.08 | 15.08 | 15.08 | 22.8 |
| (Humectant) | | | | |
| Dipropylene glycol | 3.5 | 3.5 | 3.5 | 3.5 |
| (Preservative) | | | | |
| Phenoxyethanol | 0.35 | 0.35 | 0.35 | 0.35 |
| Combination ratio (B):(A) | 1.6:8.4 | 1.6:8.4 | 1.6:8.4 | 1.6:8.4 |
| (1) Precipitation of wax (2W) | ⊚ | ⊚ | ⊚ | X |
| (2) Lustrous finish | ⊚ | ⊚ | ⊚ | ⊚ |
| (3) Irregularity-correcting effect | ○ | ○ | ○ | ○ |
| (4) Hardness | 85 | 85 | 40 | 60 |

* As the silicone-treated mid-sized titanium oxide particle and the silicone resin coated mid-sized titanium oxide in Table 4, silicone-treated, spindle-shaped fine titanium oxide particles having a mean minor-axis length of a primary particle of 0.03 to 0.04 μm, a mean major-axis length of a primary particle of 0.09 to 0.10 μm, and an aspect ratio (major axis/minor axis) of 2 to 4 was used.

(Production Method)

Diphenylsiloxy phenyl trimethicone and a (dimethicone/phenyl vinyl dimethicone) crosspolymer was mixed with the oil components other than diphenylsiloxy phenyl trimethicone. The resulting mixture was mixed with a wax that was melted by heating, in which a powder was dispersed, by stirring. The resulting mixture was emulsified with a mixture of other components to give a solid emulsified cosmetic.

As shown in Table 4, in Test Example 4-1, in which silicone-treated titanium oxide was blended, and in Test Example 4-2, in which silicone resin-coated titanium oxide was blended, the hardness of the solid emulsified cosmetic was improved without affecting the evaluations (1) to (3).

Also, although the improvement in hardness in Test Example 4-3, in which stearic acid-treated titanium oxide was blended, was not as great as that observed in Test Examples 4-1 and 4-2, the product was hard enough as a solid emulsified cosmetic, and also, inhibition of recrystallization of wax was excellent.

Meanwhile, in Test Example 4-4, in which no hydrophobically-treated mid-sized titanium oxide particle was blended, recrystallization of wax was observed.

Accordingly, it is preferable to incorporate a hydrophobically-treated mid-sized powder particle in terms of inhibiting recrystallization of wax, and the hardness of the solid emulsified cosmetic can be further increased by using silicone in the hydrophobic treatment.

Hereinbelow, Formulation Examples of the solid emulsified cosmetic of the present invention will be shown; however, the present invention is not limited thereto. The blending amounts of the components are all indicated by % by mass Formulation Example 1

Solid Foundation

| (Component) | (% by mass) |
|---|---|
| (1) Diphenylsiloxy phenyl trimethicone | 8.82 |
| (2) Diphenyl dimethicone (KF-54 manufactured by Shin-Etsu Chemical Co., Ltd.) | 8.82 |
| (3) Decamethylcyclopentasiloxane | 30.65 |
| (4) PEG-10 dimethicone | 2 |
| (5) Sorbitan sesquiisostearate | 1 |
| (6) Distearyldimonium chloride | 0.2 |

-continued

| (Component) | (% by mass) |
| --- | --- |
| (7) Palmitic acid | 0.15 |
| (8) Tocopherol | 0.02 |
| (9) (Dimethicone/phenyldimethicone) crosspolymer (KSG-18A manufactured by Shin-Etsu Chemical Co., Ltd.) | 3.36 |
| (10) Microcrystalline wax | 0.8 |
| (11) Paraffin wax | 3.5 |
| (12) Silicone-treated iron oxide | 2.75 |
| (13) Silicone-treated pigment-grade titanium oxide | 12 |
| (14) Silicone-treated mid-sized titanium oxide (silicone-treated, spindle-shaped fine titanium oxide particle having a mean miner-axis length of a primary particle of 0.03 to 0.04 μm, a mean major-axis length of a primary particle of 0.09 to 0.10 μm, and an aspect ratio (major axis/minor axis) of 2 to 4) | 7 |
| (15) Deionized water | 15.08 |
| (16) Dipropylene glycol | 3.5 |
| (17) Phenoxyethanol | 0.35 |

(Production Method)

The components (1), (2), and (9) were blended into (3). The resulting mixture was mixed with (10) and (11) that were melted by heating, in which (12) to (14) were dispersed, by stirring. The resulting mixture was emulsified with a mixture of other components to give a solid foundation.

Formulation Example 2

Solid Foundation

| (Component) | (% by mass) |
| --- | --- |
| (1) Diphenylsiloxy phenyl trimethicone | 8.82 |
| (2) Caprylyl methicone (FZ-3196 manufactured by Dow Corning Toray Co., Ltd.) | 8.82 |
| (3) Decamethylcyclopentasiloxane | 30.65 |
| (4) PEG-10 dimethicone | 2 |
| (5) Sorbitan sesquiisostearate | 1 |
| (6) Distearyldimonium chloride | 0.2 |
| (7) Palmitic acid | 0.15 |
| (8) Tocopherol | 0.02 |
| (9) (Dimethicone/phenyldimethicone) crosspolymer (KSG-18A manufactured by Shin-Etsu Chemical Co., Ltd.) | 3.36 |
| (10) Microcrystalline wax | 0.8 |
| (11) Paraffin wax | 3.5 |
| (12) Silicone-treated iron oxide | 2.75 |
| (13) Silicone-treated pigment-grade titanium oxide | 12 |
| (14) Silicone-treated mid-sized titanium oxide (silicone-treated spindle-shaped fine titanium oxide particle having a mean miner-axis length of a primary particle of 0.03 to 0.04 μm, a mean major-axis length of a primary particle of 0.09 to 0.10 μm, and an aspect ratio (major axis/minor axis) of 2 to 4) | 7 |
| (15) Deionized water | 15.08 |
| (16) Dipropylene glycol | 3.5 |
| (17) Phenoxyethanol | 0.35 |

(Production Method)

The components (1), (2), and (9) were blended into (3). The resulting mixture was mixed with (10) and (11) that were melted by heating, in which (12) to (14) were dispersed, by stirring. The resulting mixture was emulsified with a mixture of other components to give a solid foundation.

No recrystallization of wax was observed after two weeks of acceleration test, and an excellent lustrous finish and an excellent irregularity-correcting effect were achieved in both of the solid emulsified cosmetics according to the Formulation Examples 1 and 2.

What is claimed is:

1. A solid emulsified cosmetic comprising:
   (A) 4 to 18% by mass of a high refractive index silicone oil with a refractive index of 1.45 or higher at 25° C.,
   (B) a (dimethicone/phenyl vinyl dimethicone) crosspolymer,
   (C) a hydrophobic or hydrophobically-treated powder, and
   (D) a wax.

2. The solid emulsified cosmetic according to claim 1, wherein (A) the high refractive index silicone oil is selected from the group consisting of methyl phenyl silicon, caprylyl methicone, and combinations thereof.

3. The solid emulsified cosmetic according to claim 1 wherein a ratio (B):(A) is 1:9 to 3:7.

4. The solid emulsified cosmetic according to claim 2, wherein (A) the high refractive index silicone oil is present in an amount of 8 to 18% by mass.

5. The solid emulsified cosmetic according to claim 1, wherein (C) the hydrophobic or hydrophobically-treated powder is a silicone-treated powder.

6. The solid emulsified cosmetic according to claim 5, wherein a mean major-axis length of a primary particle of (C) the hydrophobic or hydrophobically-treated powder is 0.05 to 0.2 μm.

7. A method for imparting a lustrous finish and an irregularity-correcting effect to a solid emulsified cosmetic, comprising:
blending
(A) 4 to 18% by mass of a high refractive index silicone oil with a refractive index of 1.45 or higher at 25° C.,
(B) a (dimethicone/phenyl vinyl dimethicone) crosspolymer,
(C) a hydrophobic or hydrophobically-treated powder, and
(D) a wax
into the solid emulsified cosmetic.

8. The solid emulsified cosmetic according to claim 2, wherein (C) the hydrophobic or hydrophobically-treated powder is a silicone-treated powder.

9. The solid emulsified cosmetic according to claim 8, wherein a mean major-axis length of a primary particle of the silicone-treated powder is 0.05 to 0.2 μm and wherein a specific surface area of the silicone-treated powder is between 10 m$^2$/g and 150 m$^2$/g.

10. The solid emulsified cosmetic according to claim 2, wherein (A) the high refractive index silicone oil is methyl phenyl silicone and wherein the methyl phenyl silicone is diphenylsiloxy phenyl trimethicone.

11. The solid emulsified cosmetic according to claim 1, wherein (B) the (dimethicone/phenyl vinyl dimethicone) crosspolymer has a refractive index of 1.40 or higher at 25° C.

12. The solid emulsified cosmetic according to claim 11, wherein (B) the (dimethicone/phenyl vinyl dimethicone) crosspolymer is present in the amount of from 0.3 to 6% by mass.

13. The solid emulsified cosmetic according to claim 8, wherein the silicone-treated powder is silicone-treated titanium oxide powder.

14. The solid emulsified cosmetic according to claim 13, wherein a ratio (silicone-treated titanium oxide powder):(A) is about 0.01:1.7.

15. The solid emulsified cosmetic according to claim 1, wherein (D) the wax is present in the amount from 1 to 8% by mass.

16. The solid emulsified cosmetic according to claim 1, further comprising an oil from about 5 to 50% by mass, selected from the group consisting of hydrocarbon oil, higher fatty acid, higher alcohol, synthetic ester oil, silicone oil, liquid oil, solid oil, and combinations thereof.

17. The method according to claim 7, wherein blending comprises:
mixing (A) the high refractive index silicone oil and (B) the (dimethicone/phenyl vinyl dimethicone) crosspolymer to form a gel;
melting (D) the wax; and
emulsifying the gel in the melted wax.

18. A solid emulsified cosmetic comprising:
(A) a silicone oil,
(B) a (dimethicone/phenyl vinyl dimethicone) crosspolymer, and
(C) a hydrophobic or hydrophobically-treated powder.

19. The solid emulsified cosmetic according to claim 18, wherein (A) the silicone oil is diphenylsiloxy phenyl trimethicone having a refractive index of 1.45 or higher at 25° C., and is present in the amount from 4 to 18% by mass.

20. The solid emulsified cosmetic according to claim 18, wherein the (C) the hydrophobic or hydrophobically-treated powder is a silicone-treated titanium oxide powder having a mean major-axis length of a primary particle of the silicone-treated powder is 0.05 to 0.2 μm and wherein a specific surface area of the silicone-treated powder is between 10 m$^2$/g and 150 m2/g.

* * * * *